US012669497B2

(12) United States Patent
Krusemark et al.

(10) Patent No.: US 12,669,497 B2
(45) Date of Patent: Jun. 30, 2026

(54) AFFINITY LABELING OF DNA-LINKED LIGANDS FOR HIGH THROUGHPUT LIGAND BINDING ASSAYS AND THE USES THEREOF

(71) Applicant: Purdue Research Foundation, West Lafayette, IN (US)

(72) Inventors: Casey J. Krusemark, West Lafayette, IN (US); Bo Cai, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 1326 days.

(21) Appl. No.: 17/472,756

(22) Filed: Sep. 13, 2021

(65) Prior Publication Data

US 2022/0098643 A1 Mar. 31, 2022

Related U.S. Application Data

(60) Provisional application No. 63/083,445, filed on Sep. 25, 2020.

(51) Int. Cl.
*G01N 33/53* (2006.01)
*C12Q 1/48* (2006.01)
*C12Q 1/686* (2018.01)

(52) U.S. Cl.
CPC ......... *G01N 33/5308* (2013.01); *C12Q 1/485* (2013.01); *C12Q 1/686* (2013.01)

(58) Field of Classification Search
None
See application file for complete search history.

(56) References Cited

PUBLICATIONS

Denton et al., "Crosslinking of DNA-linked ligands to target proteins for enrichment from DNA-encoded libraries," Med. Chem. Commun. 2016, 7:2020-2027. (Year: 2016).*
Cai et al., "Selection of DNA-Encoded Libraries to Protein Targets within and on Living Cells," J. Am. Chem. Soc. 2019, 141:17057-17061. (Year: 2019).*
Liu, R., Li, X., & Lam, K. S. (2017). Combinatorial chemistry in drug discovery. Current opinion in chemical biology, 38, 117-126.
Goodnow, Jr, R. A., Dumelin, C. E., & Keefe, A. D. (2017). DNA-encoded chemistry: enabling the deeper sampling of chemical space. Nature Reviews Drug Discovery, 16, 131.
Mahendrarajah, K., Dalby, P. A., Wilkinson, B., Jackson, S. E., & Main, E. R. (2011). A high-throughput fluorescence chemical denaturation assay as a general screen for protein-ligand binding. Analytical biochemistry, 411, 155-157.
Gesmundo, N. J., Sauvagnat, B., Curran, P. J., Richards, M. P., Andrews, C. L., Dandliker, P. J., & Cernak, T. (2018). Nanoscale synthesis and affinity ranking. Nature, 557, 228-232.
Stuckey, J. I., Dickson, B. M., Cheng, N., Liu, Y., Norris, J. L., Cholensky, S. H., . . . & Black, K. (2016). A cellular chemical probe targeting the chromodomains of Polycomb repressive complex 1. Nature chemical biology, 12, 180-187.
Degorce, F., Card, A., Soh, S., Trinquet, E., Knapik, G. P., & Xie, B. (2009). HTRF: a technology tailored for drug discovery—a review of theoretical aspects and recent applications. Current chemical genomics, 3, 22-32.
Neri, D., & Lemer, R. A. (2018). DNA-encoded chemical libraries: A selection system based on endowing organic compounds with amplifiable information. Annual review of biochemistry, 87, 479-502.
Annis, D. A., Nazef, N., Chuang, C. C., Scott, M. P., & Nash, H. M. (2004). A general technique to rank protein-ligand binding affinities and determine allosteric versus direct binding site competition in compound mixtures. Journal of the American Chemical Society, 126, 15495-15503.
Kim, D., Jetson, R. R., & Krusemark, C. J. (2017). A DNA-assisted immunoassay for enzyme activity via a DNA-linked, activity-based probe. Chemical Communications, 53(68), 9474-9477.
Jetson, R. R., & Krusemark, C. J. (2016). Sensing Enzymatic Activity by Exposure and Selection of DNA-Encoded Probes. Angewandte Chemie, 128(33), 9714-9718.
Rectenwald, J. M., Hardy, P. B., Norris-Drouin, J. L., Cholensky, S. H., James, L. I., Frye, S. V., & Pearce, K. H. (2019). A general TR-FRET assay platform for high-throughput screening and characterizing inhibitors of methyl-lysine reader proteins. SLAS Discovery: Advancing Life Sciences R&D, 24, 693-700.
Grant, E.K., Fallon, D.J., Eberl, H.C., Fantom, K.G., Zappacosta, F., Messenger, C., Tomkinson, N.C. & Bush, J.T. (2019). A photoaffinity displacement assay and probes to study the cyclin-dependent kinase family. Angewandte Chemie International Edition, 58(48), 17322-17327.
Catalano, M., Oehler, S., Prati, L., Favalli, N., Bassi, G., Scheuermann, J., & Neri, D. (2020). Complexation with a cognate antibody fragment facilitates affinity measurements of fluorescein-linked small molecule ligands. Analytical Chemistry, 92, 10822-10829.
Prati, L., Bigatti, M., Donckele, E. J., Neri, D., & Samain, F. (2020). On-DNA hit validation methodologies for ligands Identified from DNA-encoded chemical libraries. Biochemical and Biophysical Research Communications. https://doi.org/10.1016/j.bbrc.2020.04.030.

(Continued)

*Primary Examiner* — Kaijiang Zhang
(74) *Attorney, Agent, or Firm* — Purdue Research Foundation

(57) ABSTRACT

The present application relates to an assay method using affinity crosslinking of DNA-linked ligands to proteins to enable small molecule screening and determination of apparent affinity constants of ligands to the proteins. This method has been applied to determine 96 compounds' dissociation constants to a protein target simultaneously, and directly determine a compound's $IC_{50}$ against five protein targets concurrently in crude cell lysates. Additionally, this approach was used to screen a Library of Pharmacologically Active Compounds (LOPAC) library against dihydrofolate reductase (eDHFR), enabling the discovery of a novel eDHFR inhibitor (IC50=7.9 μM). An assay kit and the method of uses are within the scope of this disclosure.

10 Claims, 10 Drawing Sheets

(56) References Cited

PUBLICATIONS

Denton, K. E., & Krusemark, C. J. (2016). Crosslinking of DNA-linked ligands to target proteins for enrichment from DNA-encoded libraries. MedChemComm, 7, 2020-2027.

Denton, K. E., Wang, S., Gignac, M. C., Milosevich, N., Hof, F., Dykhuizen, E. C., & Krusemark, C. J. (2018). Robustness of in vitro selection assays of DNA-encoded peptidomimetic ligands to CBX7 and CBX8. SLAS Discovery: Advancing Life Sciences R&D, 23, 417-428.

Cai, B., Kim, D., Akhand, S., Sun, Y., Cassell, R. J., Alpsoy, A. & Krusemark, C. J. (2019). Selection of DNA-encoded libraries to protein targets within and on living cells. Journal of the American Chemical Society, 141, 17057-17061.

* cited by examiner

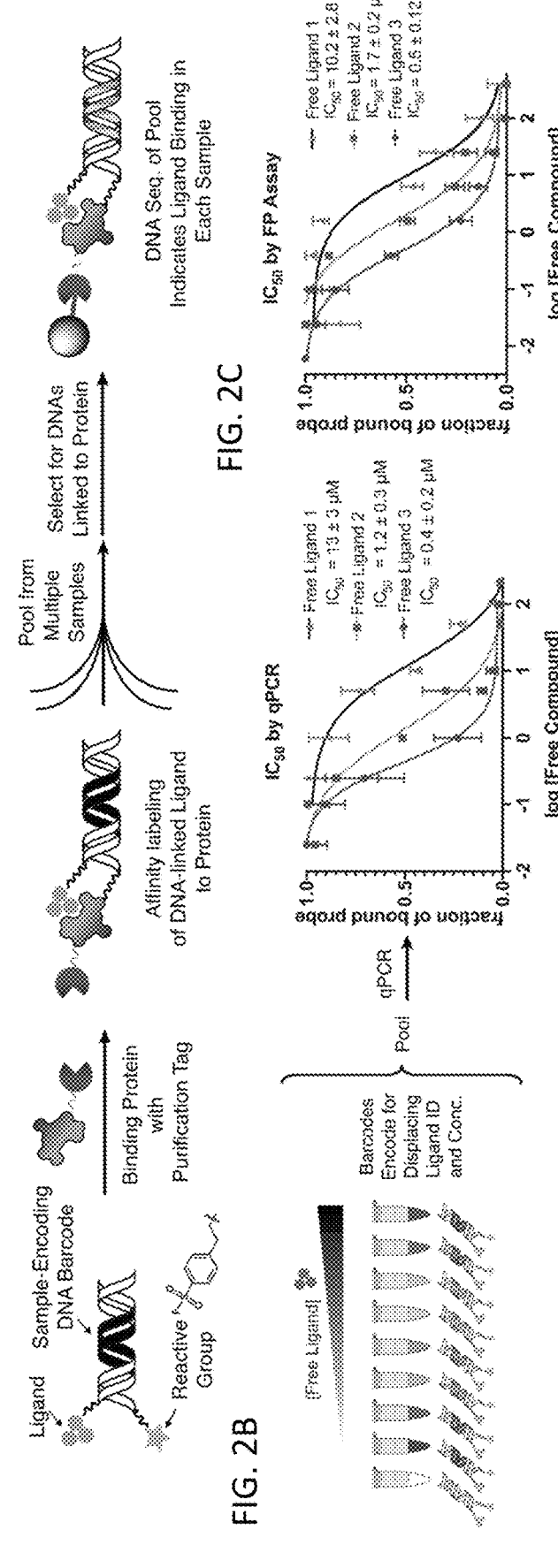

| Compound | Structure |
|---|---|
| (1) | |
| (2) | |
| (3) | |
| (4) | |

FIG. 3A

AFFINITY LABELING OF DNA-LINKED LIGANDS FOR HIGH THROUGHPUT LIGAND BINDING ASSAYS AND THE USES THEREOF

CROSS-REFERENCE TO RELATED APPLICATIONS

This present U.S. patent application relates to and claims the priority benefit of U.S. Provisional Patent Application Ser. No. 63/083,445, filed Sep. 25, 2020, the contents of which are hereby incorporated by reference in its entirety into this disclosure.

GOVERNMENT SUPPORT CLAUSE

This invention was made with government support under a grant GM128894-01 awarded by the National Institutes of Health. The government has certain rights in the invention.

TECHNICAL FIELD

The present application relates to an assay method for detecting ligand protein binding that are useful for performing high throughput screening in drug discovery using DNA sequencing or qPCR as the readout with low cost and high sensitivity.

BACKGROUND

This section introduces aspects that may help facilitate a better understanding of the disclosure. Accordingly, these statements are to be read in this light and are not to be understood as admissions about what is or is not prior art.

The identification and characterization of small molecule ligands to specific protein targets is central to the discovery of drugs and chemical probes[1-3]. While a variety of experimental approaches are available for directly analyzing protein-ligand interactions (e.g. fluorescence polarization (FP)[4], the amplified luminescent proximity homogeneous assay (AlphaScreen)[5], and time-resolved fluorescence resonance energy transfer (TR-FRET)[6]), significant limitations still exist. The FP assay platform is widely applied, but this approach can be limited by the need for a high affinity labeled ligand and/or compounds with inherent fluorescent or absorbance properties[7]. In many cases, FP requires high concentrations of target protein that cannot be readily achieved or is cost prohibitive[8]. Additionally, as the results of an FP assay are largely dependent on the probe's $K_d$, this can be a problem for identifying weak interactions[9]. The main disadvantage of the AlphaScreen platform is its sensitivity to ambient light and the requirement of high-energy laser excitation source[10]. While TR-FRET enables homogeneous binding assays, the requirement of two labels and the extra cost of the equipment and reagents in these assays are the main limitations[11]. Recently, Bush and coworkers reported a photoaffinity displacement assay to study the cyclin-dependent kinase family[12]. The Neri group reported ELISA-inspired methods to measure small molecule's affinity to protein targets[13]. There are unmet needs for drug discovery assays with both a high sensitivity and a low cost.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein:

FIG. 1A shows LDA for compounds' IC50 determination. FIG. 1B shows DNA-based crosslinking assay for the determination of ligands' Kd values.

FIGS. 2A-2H show the application of LDA in quantifying compounds' IC50 and screening. FIG. 2A shows the structures of tested compounds. IC50 of compound 1-3 determined by LDA (FIG. 2B) and FP assay (FIG. 2C). FIG. 2D shows determination of BrBA's IC50 to five protein targets in one pot. FIG. 2E shows the assessment of the robustness of LDA. FIG. 2F shows the screening of LOPAC library against eDHFR using LDA. DNA samples with read numbers below 2 in sequencing were excluded. FIG. 2G shows the validation of novel hit (GW1929) by FP assay. FIG. 2H shows GW1929's activity towards hDHFR enzyme.

FIGS. 3A-3G depict the DNA-based cross-linking assay for the determination of ligands' Kd values to CBX7-ChD. FIG. 3A shows the structures of tested compounds. FIG. 3B shows Kd of compound (1)-(4) determined by DNA-based cross-linking approach. FIG. 3C shows the measurement of the Kd of pure and "contaminated" compound d to CBX7-ChD. FIG. 3D shows Kd of Representative 8 compounds in the PSL. FIG. 3E shows the model (red dots) and actual experimental (blue dots) scatter plot of normalized enrichment-Kd values. FIG. 3F shows the correlation plot between off-DNA Kd of purified compounds and on-DNA Kd of crude library members. FIG. 3G shows the correlation plot between off-DNA Kd of purified compounds and on-DNA enrichment of crude library members.

DETAILED DESCRIPTION

Figure 1A:
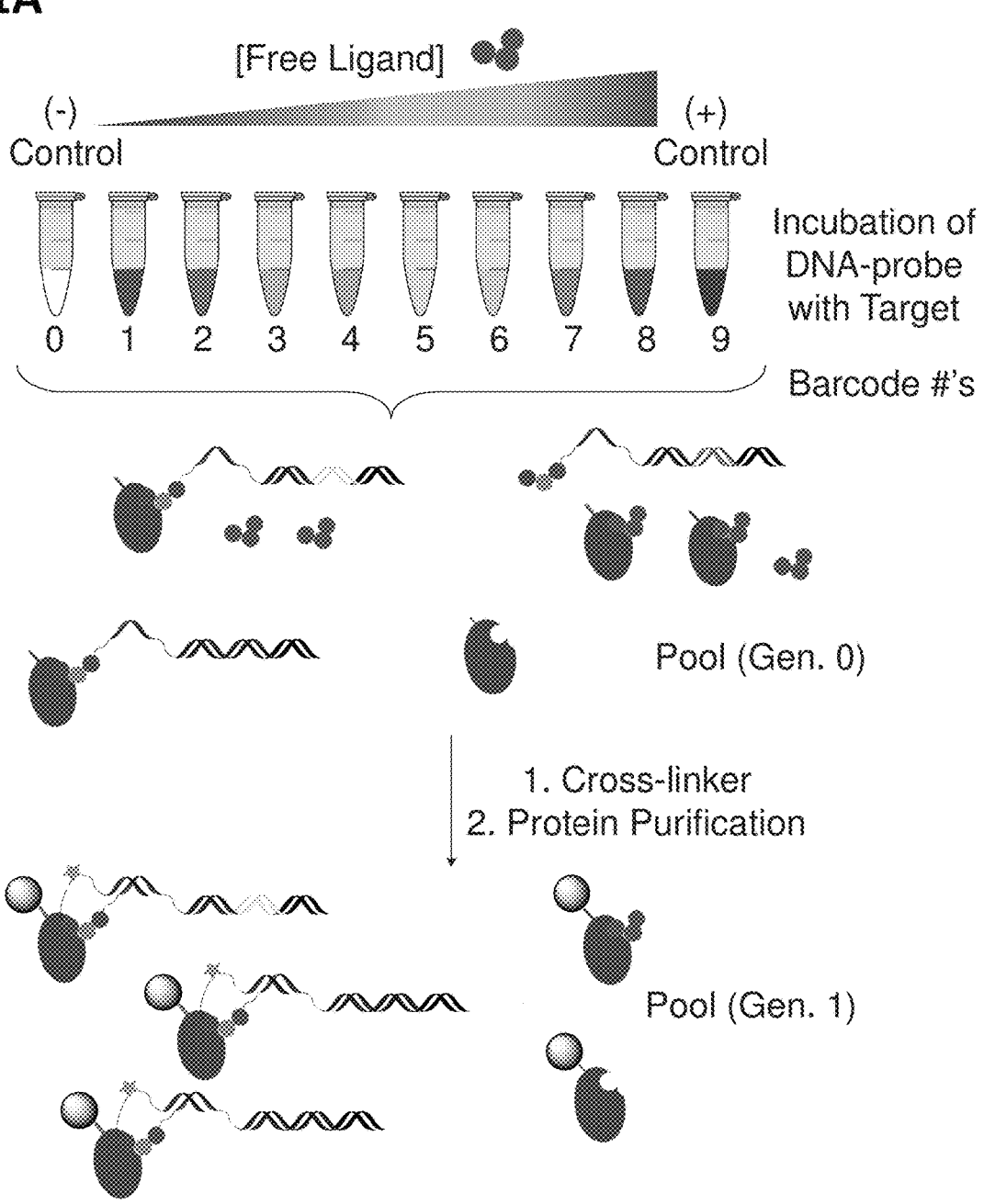
FIGS. 1A-1B depict Affinity Labeling of DNA-linked Ligands for High Throughput Ligand Binding Assays.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

In some illustrative embodiments, this disclosure relates to a diagnostic assay kit for small molecule screening to determine apparent affinity constant of a small molecule ligand through ligand displacement comprising a DNA-linked probe, a complementary DNA-linked cross-linker, a free ligand, and a target protein of interest, wherein said DNA-linked probe comprises a known protein ligand and an electrophilic or photoreactive crosslinker appended at the 5' or 3' end of an encoding DNA; wherein said protein ligand and said electrophilic or photoreactive crosslinker locate together on one end of said encoding DNA or separately on either 5' or 3' end; and wherein said crosslinker can be one part of said ligand or linked to said ligand via a chemical linker.

In one embodiment, this disclosure relates to a diagnostic assay kit for small molecule screening to determine apparent affinity constant of a small molecule ligand through ligand displacement comprising a DNA-linked probe, a complementary DNA-linked cross-linker, a free ligand, and a target protein of interest, wherein said DNA-linked probe comprises a known protein ligand appended at the 5' end of an encoding DNA along with an electrophilic or photoreactive crosslinker opposite to the ligand on the 3' end.

In another embodiment, this disclosure relates to a diagnostic assay kit for small molecule screening to determine apparent affinity constant of a small molecule ligand through ligand displacement comprising a DNA-linked probe, a complementary DNA-linked cross-linker, a free ligand, and a target protein of interest, wherein said ligand may be on the 3' end and the crosslinker on the 5' end.

Yet in another embodiment, this disclosure relates to a diagnostic assay kit for small molecule screening to determine apparent affinity constant of a small molecule ligand through ligand displacement comprising a DNA-linked probe, a complementary DNA-linked cross-linker, a free ligand, and a target protein of interest, wherein the ligand and crosslinker may be attached to the DNA together on either end of the DNA strand.

Yet in another embodiment, this disclosure relates to a diagnostic assay kit for small molecule screening to determine apparent affinity constant of a small molecule ligand through ligand displacement comprising a DNA-linked probe, a complementary DNA-linked cross-linker, a free ligand, and a target protein of interest, wherein the crosslinker may be part of the ligand itself or be presented adjacent to the ligand via a linker to facilitate linkage to said target protein.

In some illustrative embodiments, this disclosure relates to a diagnostic assay kit for small molecule screening to determine apparent affinity constant of a small molecule ligand through ligand displacement as disclosed herein, wherein said variation of the concentration of the target protein of interest or the free ligand results in a dose dependent variation in crosslinking yield, which enables the determination of the apparent affinity constant of said ligand by curve fitting of the data because the crosslinking yield is proportional to the affinity constant of the ligands.

In some illustrative embodiments, this disclosure relates to a diagnostic assay kit for small molecule screening to determine apparent affinity constant of a small molecule ligand through ligand displacement as disclosed herein, wherein said assay kit is capable of being configured for simultaneous determination of a plurality of compounds' dissociation constants to a protein target.

In some illustrative embodiments, this disclosure relates to a diagnostic assay kit for small molecule screening to determine apparent affinity constant of a small molecule ligand through ligand displacement as disclosed herein, wherein said assay kit is capable of being configured for direct determination of a compound's IC50 against multiple protein targets simultaneously.

In some illustrative embodiments, this disclosure relates to a diagnostic assay kit for small molecule screening to determine apparent affinity constant of a small molecule ligand through ligand displacement as disclosed herein, wherein said assay kit is capable of being configured for direct determination of a compound's IC50 against multiple protein targets simultaneously in a crude cell lysate.

In some illustrative embodiments, this disclosure relates to a diagnostic assay kit for small molecule screening to determine apparent affinity constant of a small molecule ligand through ligand displacement as disclosed herein, wherein said assay kit is capable of being configured for determination of a plurality of compounds' dissociation constants to a protein target simultaneously, and direct determination of a compound's IC50 against multiple protein targets all at once in a crude cell lysate.

In some illustrative embodiments, this disclosure relates to a diagnostic assay kit for small molecule screening to determine apparent affinity constant of a small molecule ligand through ligand displacement as disclosed herein, wherein said assay kit is capable of being configured for high throughput screening, generation of structure-activity relationships, and development of selective chemical probes with a high sensitivity.

In some illustrative embodiments, this disclosure relates to a product of the diagnostic assay kit for small molecule screening to determine apparent affinity constant of a small molecule ligand through ligand displacement as disclosed herein.

In some other illustrative embodiments, this disclosure relates to an assay method for small molecule screening to determine apparent affinity constant of a small molecule ligand through ligand displacement comprising a DNA-linked probe, a complementary DNA-linked cross-linker, a free ligand, and a target protein of interest, wherein said DNA-linked probe comprises a known protein ligand and an electrophilic or photoreactive crosslinker appended at the 5' or 3' end of an encoding DNA; wherein said protein ligand and said electrophilic or photoreactive crosslinker locate together on one end of said encoding DNA or separately on either 5' or 3' end; and wherein said crosslinker can be one part of said ligand or linked to said ligand via a chemical linker.

In some other illustrative embodiments, this disclosure relates to an assay method for small molecule screening to determine apparent affinity constant of a small molecule ligand through ligand displacement comprising a DNA-linked probe, a complementary DNA-linked cross-linker, a free ligand, and a target protein of interest, wherein said DNA-linked probe comprises a known protein ligand appended at the 5' end of an encoding DNA along with an electrophilic or photoreactive crosslinker opposite to the ligand on the 3' end.

In some other illustrative embodiments, this disclosure relates to an assay method for small molecule screening to determine apparent affinity constant of a small molecule ligand through ligand displacement comprising a DNA-linked probe, a complementary DNA-linked cross-linker, a free ligand, and a target protein of interest, wherein said ligand may be on the 3' end and the crosslinker on the 5' end.

Yet in another embodiment, this disclosure relates to an assay method for small molecule screening to determine apparent affinity constant of a small molecule ligand through ligand displacement comprising a DNA-linked probe, a complementary DNA-linked cross-linker, a free ligand, and a target protein of interest, wherein the ligand and cross-linker may be attached to the DNA together on either end of the DNA strand.

Yet in another embodiment, this disclosure relates to an assay method for small molecule screening to determine apparent affinity constant of a small molecule ligand through ligand displacement comprising a DNA-linked probe, a complementary DNA-linked cross-linker, a free ligand, and a target protein of interest, wherein the crosslinker may be part of the ligand itself or be presented adjacent to the ligand via a linker to facilitate linkage to said target protein.

In some other illustrative embodiments, this disclosure relates to an assay method for small molecule screening to determine apparent affinity constant of a small molecule ligand through ligand displacement as disclosed herein, wherein variation of the concentration of the target protein of interest or the free ligand results in a dose dependent variation in crosslinking yield, which enables the determination of the apparent affinity constant of said ligand by curve fitting of the data because the crosslinking yield is proportional to the affinity constant of the ligands.

In some other illustrative embodiments, this disclosure relates to an assay method for small molecule screening to determine apparent affinity constant of a small molecule ligand through ligand displacement as disclosed herein, wherein said assay method is capable of being configured for simultaneous determination of a plurality of compounds' dissociation constants to a protein target.

In some other illustrative embodiments, this disclosure relates to an assay method for small molecule screening to determine apparent affinity constant of a small molecule ligand through ligand displacement as disclosed herein, wherein said assay method is capable of being configured for direct determination of a compound's IC50 against multiple protein targets simultaneously.

In some other illustrative embodiments, this disclosure relates to an assay method for small molecule screening to determine apparent affinity constant of a small molecule ligand through ligand displacement as disclosed herein, wherein said assay method is capable of being configured for direct determination of a compound's IC50 against multiple protein targets simultaneously in a crude cell lysate.

In some other illustrative embodiments, this disclosure relates to an assay method for small molecule screening to determine apparent affinity constant of a small molecule ligand through ligand displacement as disclosed herein, wherein said assay method is capable of being configured for determination of a plurality of compounds' dissociation constants to a protein target simultaneously, and direct determination of a compound's IC50 against multiple protein targets all at once in a crude cell lysate.

In some other illustrative embodiments, this disclosure relates to an assay method for small molecule screening to determine apparent affinity constant of a small molecule ligand through ligand displacement as disclosed herein, wherein said assay method is capable of being configured for high throughput screening campaigns, generation of structure-activity relationships, and development of selective chemical probes with a high sensitivity and a low cost.

In some other illustrative embodiments, this disclosure relates to a diagnostic assay kit manufactured according to the assay method assay as disclosed herein.

DNA-encoded chemical libraries (DELs) have recently emerged as valuable approach to ligand discovery. This approach capitalizes on the powerful tools of molecular biology for DNA manipulation and analysis. Use of DNA sequence analysis as the detection platform allows remarkable sensitivity, low sample requirements, use of widely available instrumentation, and high-level multiplexing through DNA barcoding. We previously reported two DNA-based approaches for detection of enzymatic activity by use of DNA-linked enzyme substrates or active site probes[14]. Here, we extend the use of DNA sequence analysis as a protein assay platform with a DNA-based ligand binding assay for the characterization of protein-ligand interactions. The assay requires very small amounts of protein, does not require specialized equipment, fluorescent or radioactive labels, and allows the evaluation of ligand binding and apparent protein affinity in a highly multiplexed format. To demonstrate the assay versatility, we implement the approach in both a ligand displacement assay (LDA) (FIG. 1a) amenable to small molecule screening and in a direct binding format to determine affinity constants of DNA-linked ligands (FIG. 1b) through protein titration.

Use of this approach in a ligand displacement assay involves incubation of a protein target with a DNA-linked probe, which consists of a known protein ligand appended at the 5' end of an encoding DNA along with an electrophilic crosslinker (such as a sulfonyl fluoride or N-hydroxysuccinimide ester) or a photoreactive group (diazirine, aryl azide, benzophenone) opposite to the ligand on the 3' end. This dual display format has previously shown to be effective for affinity labeling of ligand binding proteins with DNA[15]. Co-incubation with a competing free ligand will displace the DNA-linked probe, resulting in decreased affinity labeling and lower DNA recovery in a subsequent purification of the protein. High-throughput implementation of the assay involves use of DNA barcodes on the probe to encode the identity and/or the concentration of the competing free ligand.

Figure 2D:
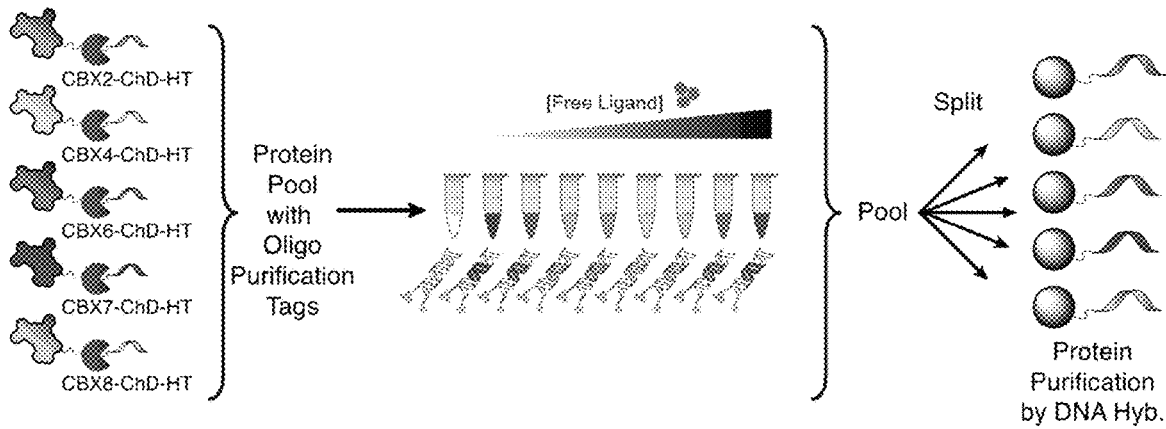
Figure 2D:
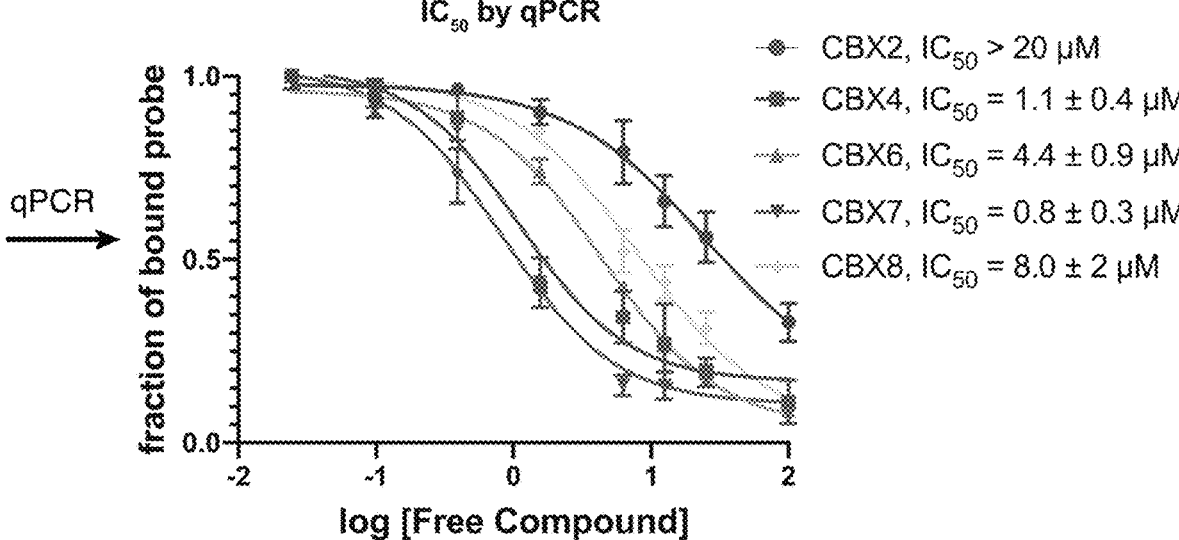

As the initial demonstration, we used the DNA-based LDA to determine $IC_{50}$ values for three compounds of varying affinity. We chose the ligands to the Halo-tagged protein Chromobox Homologue 7 Chromodomain (CBX7-ChD), as a model system (FIG. 1a). DNA-linked probes were prepared by conjugating a BrBA peptide ligand (Compound 3 in FIG. 2a, $K_d \approx 26$ nM to CBX7-ChD)[16] to different DNA encoding barcodes. As is shown in FIG. 1a, the barcodes serve to encode both the identity and the concentration of competing free ligands in a titration series. Following the incubation to allow crosslinking, labeling by the probe is quenched by addition of excess (1000×) free ligand (BrBA), and components from all samples are pooled. The target protein is then purified by chloroalkane beads. The relative recovery of each DNA-probe is determined by DNA sequencing and indicates the crosslinking yield in each sample. A dose-dependent reduction in crosslinking is observed as the concentration of free ligand increases, enabling the calculation of $IC_{50}$ values (13.3 μM, 1.2 μM and 0.4 μM, respectively, shown in FIG. 2b). To verify the results from LDA approach, we performed an FP assay with a fluorescein-labeled BrBA using the same protein and probe concentrations, which gave nearly identical results (FIG. 2c). Next, we aimed to apply LDA for the determination of the $IC_{50}$ of a ligand to 5 protein targets simultaneously. We fused Halotag to the chromodomains in the CBX family (CBX2/4/6/7/8). All five proteins demonstrated similar expression level in crude cell lysates (FIG. SX). First, each protein was pre-incubated with a unique 20-mer DNA-linked chloroalkane. After quenching with 1000× free chloroalkane, all 5 proteins were then pooled and incubated with increasing concentration of the free BrBA. Following cross-linking, each of the five proteins was incubated with its complementary DNA-linked biotin and purified by streptavidin beads. Plotting the recovery of DNA-probe enables the calculation of BrBA's $IC_{50}$ values to these five protein targets (FIG. 1d).

Figures 2E, 2F:
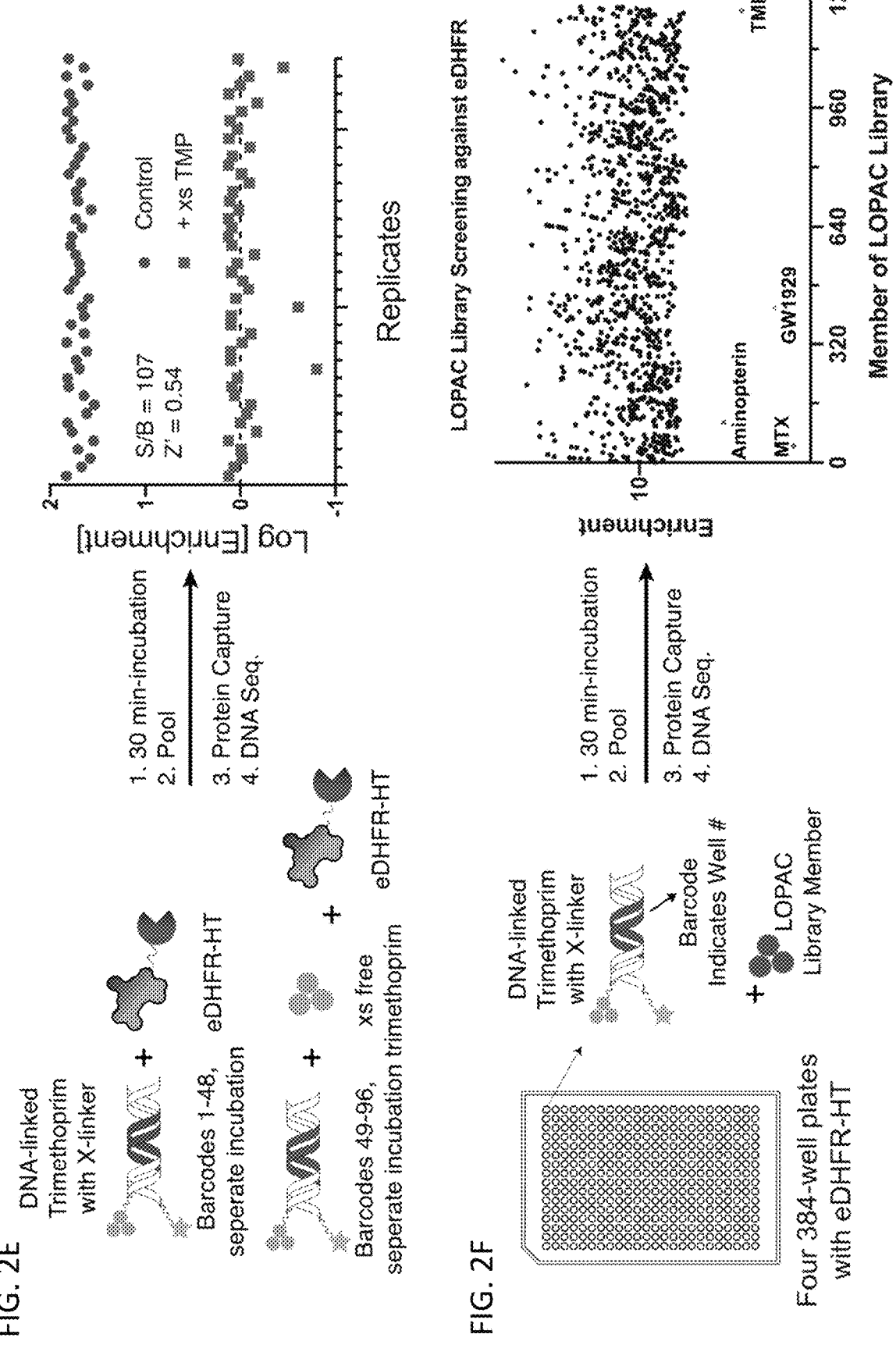
Figure 2G:
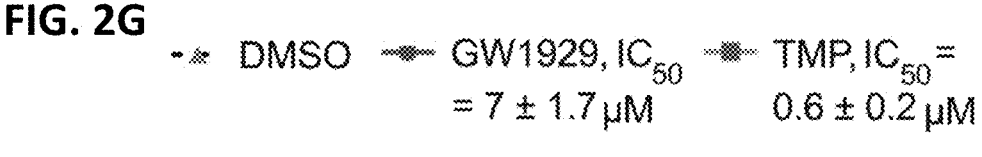
Figure 2G:
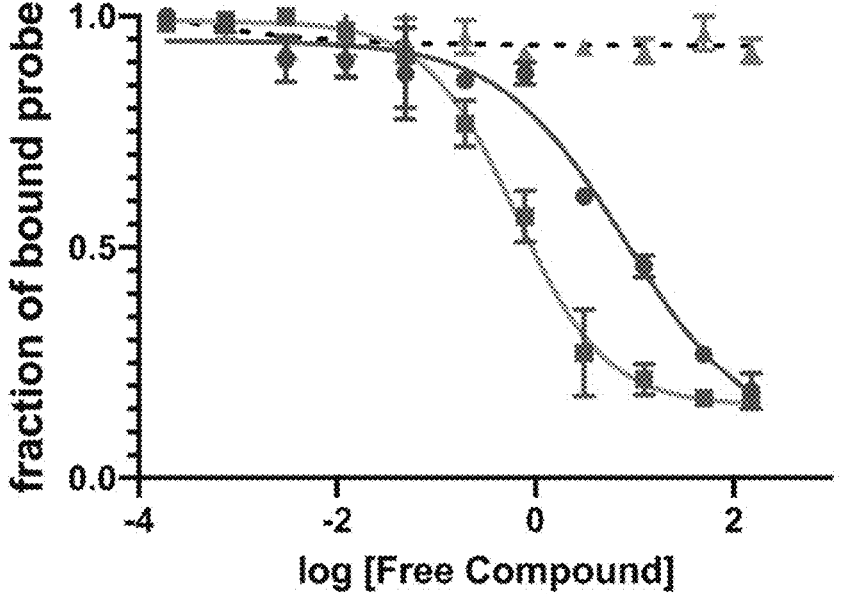
Figure 2H:
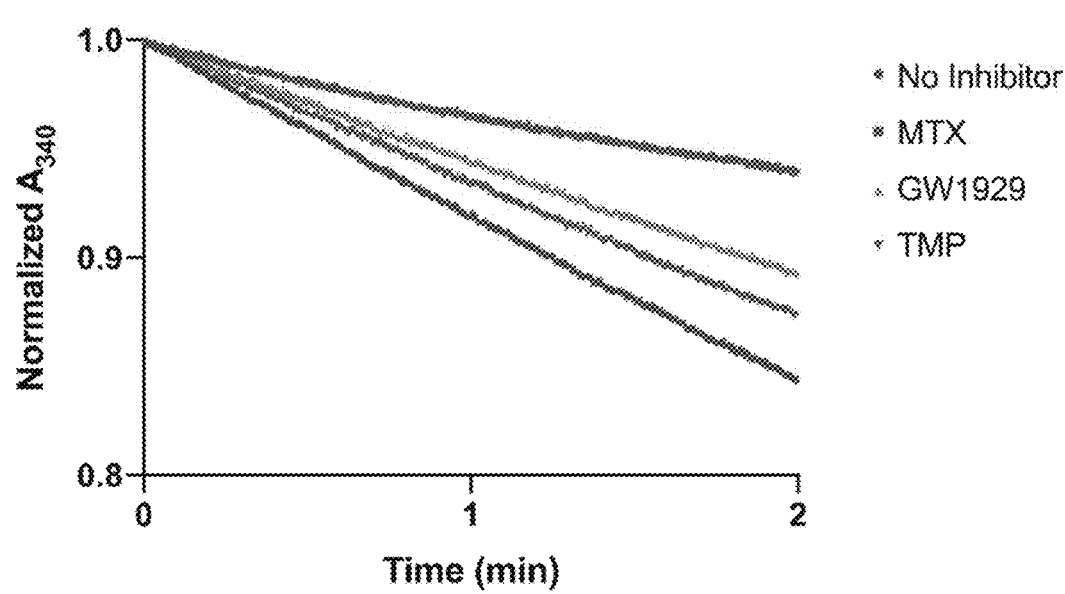

To further evaluate the robustness of this assay, we prepared 96 DNA-linked BrBA probes with unique barcodes. Half of the probes were incubated with protein and cross-linker, while the other half of the probes were additionally incubated with 1000× free ligand (BrBA). Enrichment of the probes from the two groups were well distinguished (Z' factor=0.77), indicating a robustness suitable for HTS (FIG. 1e). To further assess well-to-well variability, this experiment was repeated with separate incubation of samples in a well plate. A similar but slightly worse Z' factor (Z'=0.54, Fig. SX) was observed. We then used this approach to screen the Library of Pharmacologically Active Compounds (LOPAC) library against dihydrofolate reductase (DHFR), a therapeutic target for treating infections (FIG. 2f). Hit compounds within the library displaces the DNA-linked trimethoprim, leading to lower enrichment of the DNA-trimethoprim. All the 3 known inhibitors of DHFR and a novel compound, GW1929, showed low probe recovery. To validate the screening results, we measured the $IC_{50}$ of the novel inhibitor to DHFR, which was tested to be 7.9 μM. Due to the benefit of DNA-encoding in miniaturization, the approximate cost for the LOPAC library screening was $2000 and, at the same time, the cost does not scale appreciably with the library size, which is markedly lower than traditional screening campaigns.

Figure 1B:
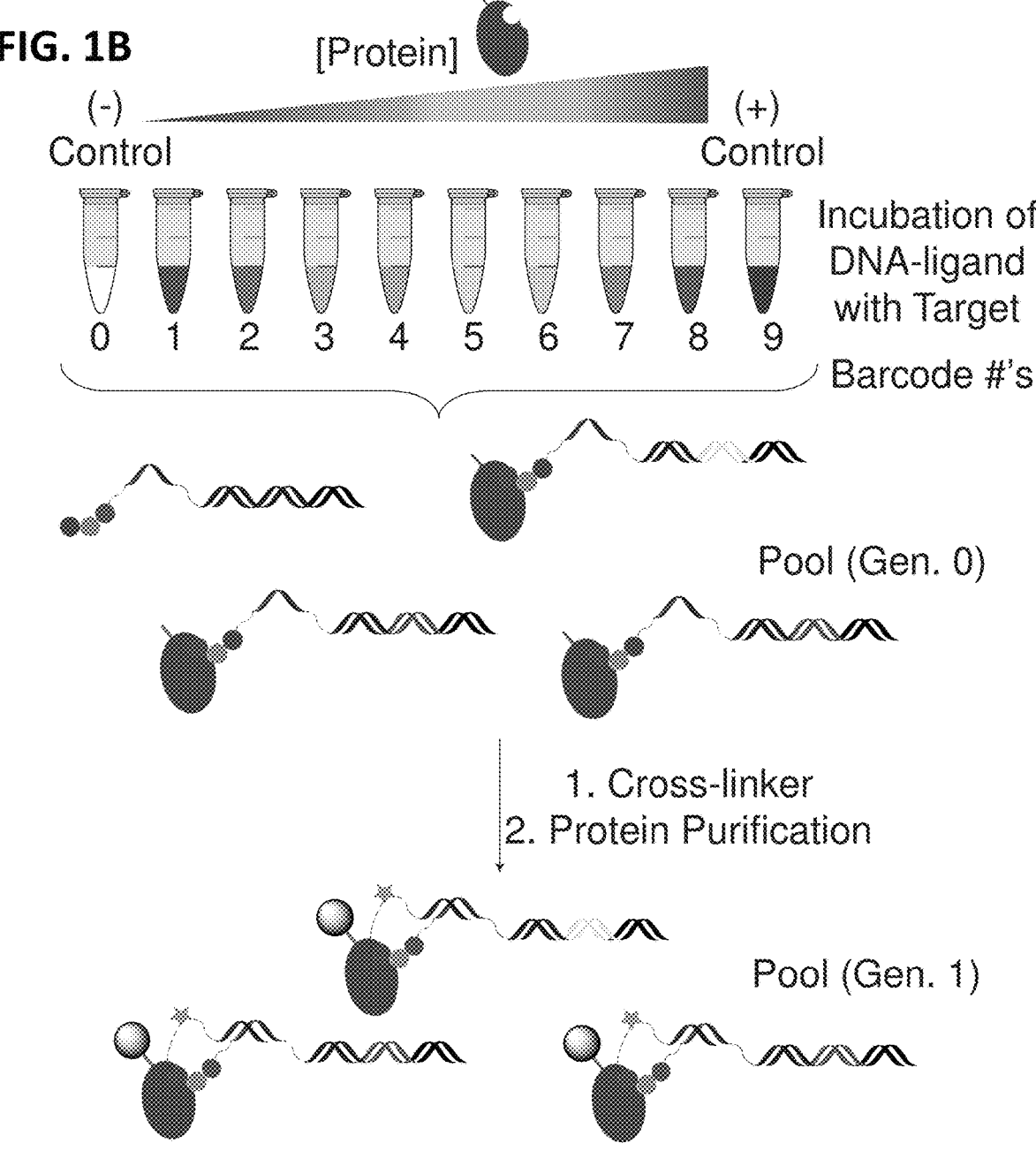
Figure 3A:
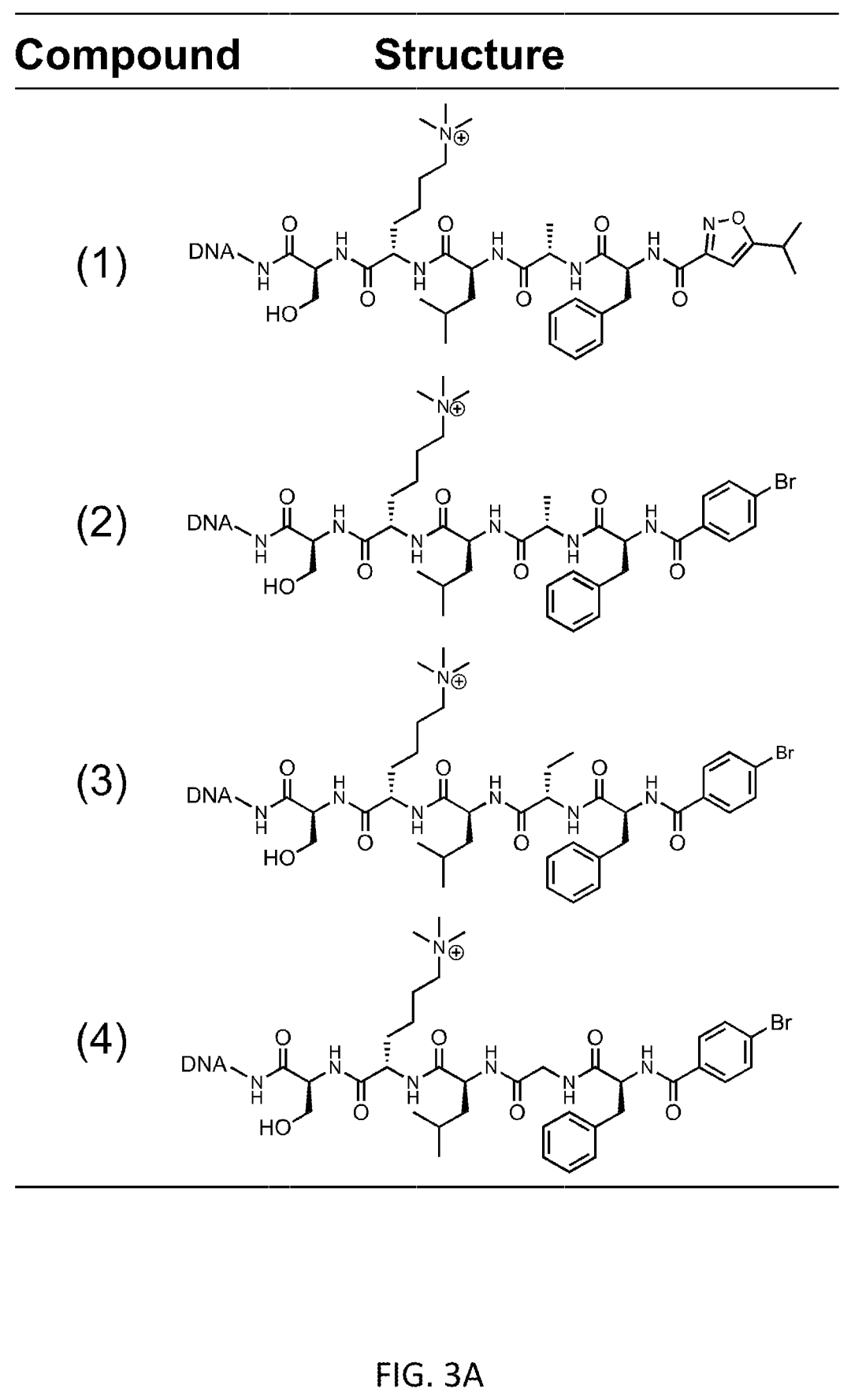
Figure 3B:
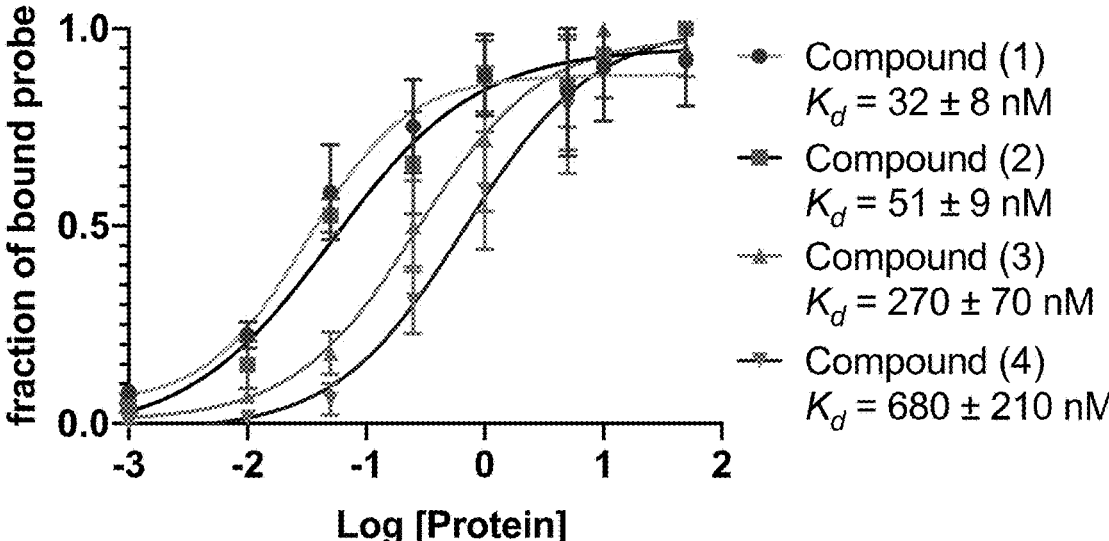

Next, we applied this approach to determine apparent $K_d$ values of several DNA-linked ligands (FIG. 1b). A ligand to be tested is conjugated to DNA that allows tethering of a crosslinking moiety on the opposite strand to enable covalent linkage to the protein target. The barcodes serve to encode both the identity of the DNA-linked ligand and also the protein concentration of a given sample within a titration series. The crosslinking yield of the DNA to the target protein is proportional to the fraction of the DNA-ligand bound to the protein, which is determined by DNA sequencing after protein purification and normalization to control samples. To demonstrate the generality of this approach, four compounds were prepared on encoding DNA scaffolds (FIG. 3a, compound (1)-(4)) with a range of affinities to CBX7-ChD. After incubation with various protein concentrations, crosslinking was quenched with excess ligand; all samples pooled; and the target protein purified. DNA sequencing of the pool gave binding curves, and the four ligands showed differential $K_d$'s to CBX7-ChD as expected (FIG. 3b).

Figure 3C:
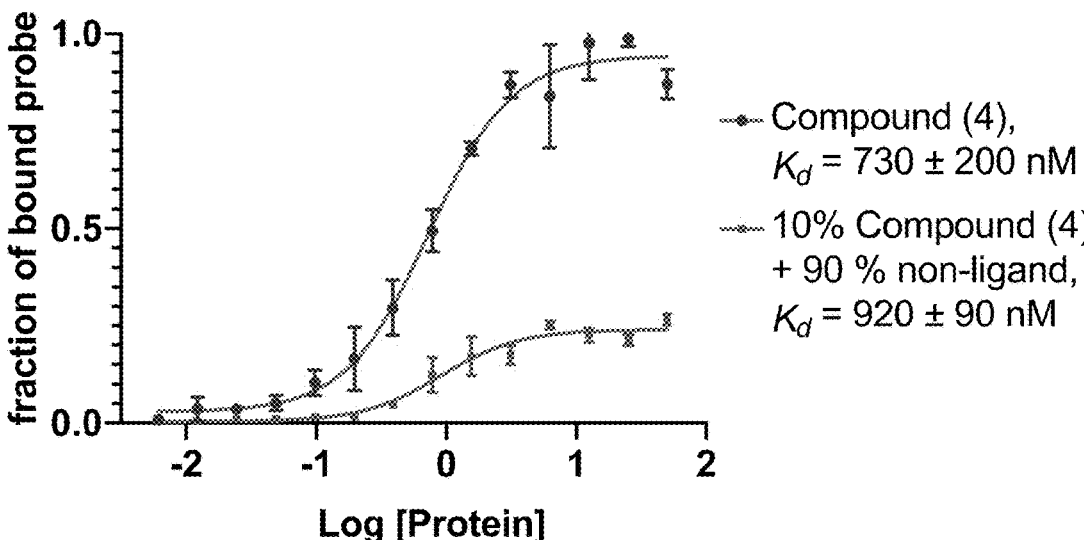

This approach has several benefits over conventional approaches for $K_d$ determination. Ligand binding assays are often conducted with the small molecule ligand in molar excess over the protein target, which then requires high purity of tested compounds. Because this approach uses the protein in excess, it can measure and rank order compounds' effective $K_d$'s without the requirement of obtaining pure compounds (provided contaminants are not ligands). This benefit can significantly improve throughput when testing multiple molecules. To demonstrate this, we compared the apparent affinity constants obtained for the DNA-conjugated compound (4) "contaminated" with a non-ligand DNA. As expected, the cross-linking yield of impure compound d was markedly lower than the pure compound, yet the effective $K_d$ values obtained were within error (FIG. 3c, 730±210 nM vs 920±90 nM).

Figures 3D, 3E:
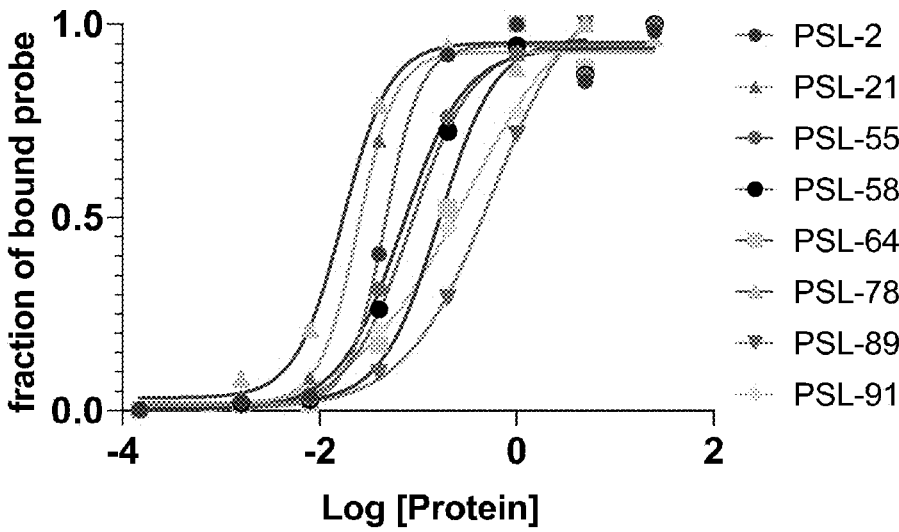

To evaluate assay performance in a highly multiplexed format, we generated a 96-member DNA-encoded library by varying 24 building blocks at each of four monomer positions within the BrBA peptide ligand (FIG. SX). We set out to measure and rank order 96 compounds' affinity constants concurrently. DNA barcodes were appended to the compounds to indicate both the compound identity and the concentration of Halo-CBX7-Chd (0.2 nM-50 μM) used in the crosslinking reaction. Using our approach, all compounds' $K_d$ values were successfully derived, with the exception of those with presumed low binding affinity (Figure SX). FIG. 3d shows binding curves of 8 representative members from the library.

Figure 3F:
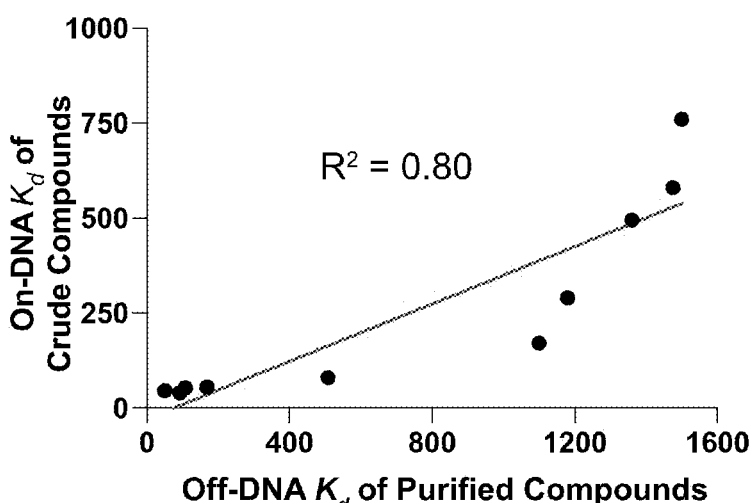
Figure 3G:
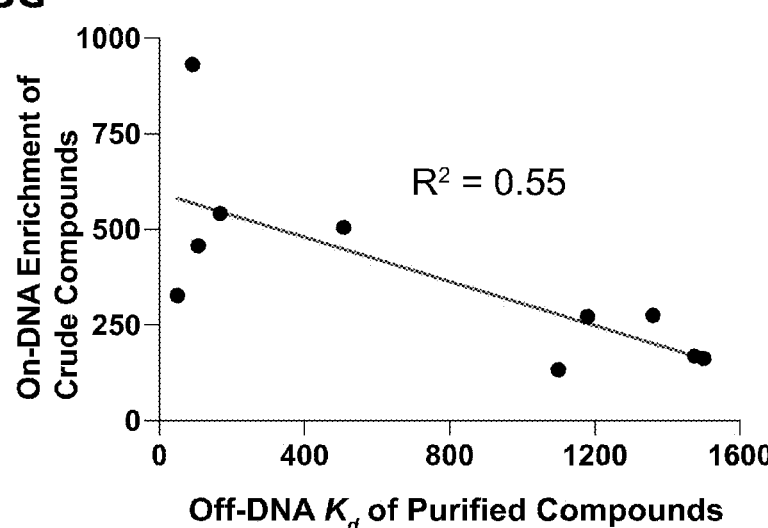

In the selection of DNA-encoded libraries for binding to protein targets, it is often assumed that enrichment values observed for a compound correlate to affinity constants. This can, however, be complicated by several factors, most notably purity. We plotted the enrichment of 96 compounds' enrichment from the selection at 250 nM of Halo-CBX7-Chd against the apparent $K_d$'s determined from the titration (blue dots in FIG. 3e). Nearly, all of the 96 compounds displayed enrichment values that are lower that would be predicted (red dots in FIG. 3e). While on-DNA synthesis of peptides is fairly robust, this result could be explained by differences in ligand purity. To verify our results, we selected compounds within the library that have been previously characterized[17], and compared their off-DNA $K_d$ values of the pure compounds determined by FP to those of the crude on-DNA compounds from our assay. The off-DNA $K_d$ of selected compounds showed a good correlation between the on-DNA $K_d$ determined by crosslinking ($R^2$=0.80, FIG. 3f), but little correlation ($R^2$=0.55, FIG. 3g) between enrichment values. This result further demonstrates that the enrichment magnitude is purity-dependent, but compound's effective $K_d$'s are less purity-dependent (provided byproducts during synthesis are non-ligands).

The affinity labeling of DNA-linked ligands enables high-level multiplexing capability in ligand binding assays, which allows the determination of hundreds of compounds' $K_d$ values to a protein target simultaneously. With DNA-barcoding, we made use of the massive miniaturization in the amounts of both chemicals and proteins required in the LOPAC library screening. We hope that the reported methodology can accelerate the generation of structure-activity relationships, development of selective chemical probes and characterization of protein-ligand interactions in drug discovery campaigns.

Those skilled in the art will recognize that numerous modifications can be made to the specific implementations described above. The implementations should not be limited to the particular limitations described. Other implementations may be possible.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

REFERENCES 1. (a) Geysen, H. M., Schoenen, F., Wagner, D., & Wagner, R. (2003). Combinatorial compound libraries for drug discovery: an ongoing challenge. Nature Reviews Drug Discovery, 2, 222-230. (b) Liu, R., Li, X., & Lam, K. S. (2017). Combinatorial chemistry in drug discovery. Current opinion in chemical biology, 38, 117-126.

2. (a) Goodnow Jr, R. A., Dumelin, C. E., & Keefe, A. D. (2017). DNA-encoded chemistry: enabling the deeper sampling of chemical space. Nature Reviews Drug Discovery, 16, 131. (b) Brenner, S., & Lerner, R. A. (1992). Encoded combinatorial chemistry. Proceedings of the National Academy of Sciences, 89, 5381-5383. (c) Neri, D., & Lerner, R. A. (2018). DNA-encoded chemical libraries: A selection system based on endowing organic compounds with amplifiable information. Annual review of biochemistry, 87, 479-502.

3. (a) Mahendrarajah, K., Dalby, P. A., Wilkinson, B., Jackson, S. E., & Main, E. R. (2011). A high-throughput fluorescence chemical denaturation assay as a general screen for protein-ligand binding. Analytical biochemistry, 411, 155-157. (b) Annis, D. A., Nazef, N., Chuang, C. C., Scott, M. P., & Nash, H. M. (2004). A general technique to rank protein-ligand binding affinities and determine allosteric versus direct binding site competition in compound mixtures. Journal of the American Chemical Society, 126, 15495-15503. (c) Gesmundo, N. J., Sauvagnat, B., Curran, P. J., Richards, M. P., Andrews, C. L., Dandliker, P. J., & Cernak, T. (2018). Nanoscale synthesis and affinity ranking Nature, 557, 228-232.

4. (a) Weber, G. (1952). Polarization of the fluorescence of macromolecules. 1. Theory and experimental method. Biochemical Journal, 51, 145. (b) Rossi, A. M., & Taylor, C. W. (2011). Analysis of protein-ligand interactions by fluorescence polarization. Nature protocols, 6, 365-387.

5. (a) Wigle, T. J., Martin Herold, J., Senisterra, G. A., Vedadi, M., Kireev, D. B., Arrowsmith, C. H., . . . & Janzen, W. P. (2010). Screening for Inhibitors of Low-Affinity Epigenetic Peptide-Protein Interactions: An AlphaScreen™-Based Assay for Antagonists of Methyl-Lysine Binding Proteins. Journal of biomolecular screening, 15, 62-71. (b) Stuckey, J. I., Dickson, B. M., Cheng, N., Liu, Y., Norris, J. L., Cholensky, S. H., . . . & Black, K. (2016). A cellular chemical probe targeting the chromodomains of Polycomb repressive complex 1. Nature chemical biology, 12, 180-187.

6. Degorce, F., Card, A., Soh, S., Trinquet, E., Knapik, G. P., & Xie, B. (2009). HTRF: a technology tailored for drug discovery—a review of theoretical aspects and recent applications. Current chemical genomics, 3, 22-32.

7. Seidler, J., McGovern, S. L., Doman, T. N., & Shoichet, B. K. (2003). Identification and prediction of promiscuous aggregating inhibitors among known drugs. J. Med. Chem., 46, 4477-4486.

8. (a) Parker, G. J., Law, T. L., Lenoch, F. J., & Bolger, R. E. (2000). Development of high throughput screening assays using fluorescence polarization: nuclear receptor-ligand-binding and kinase/phosphatase assays. Journal of Biomolecular Screening, 5, 77-88. (b) Lea, W. A., & Simeonov, A. (2011). Fluorescence polarization assays in small molecule screening. Expert opinion on drug discovery, 6, 17-32.

9. Huang, X. (2003). Fluorescence polarization competition assay: the range of resolvable inhibitor potency is limited by the affinity of the fluorescent ligand. J. Biomolecular Screening, 8, 34-38.

10. Eglen, R. M., Reisine, T., Roby, P., Rouleau, N., Illy, C., Bossé, R., & Bielefeld, M. (2008). The use of AlphaScreen technology in HTS: current status. Current chemical genomics, 1, 2-10.

11. Rectenwald, J. M., Hardy, P. B., Norris-Drouin, J. L., Cholensky, S. H., James, L. I., Frye, S. V., & Pearce, K. H. (2019). A general TR-FRET assay platform for high-throughput screening and characterizing inhibitors of methyl-lysine reader proteins. SLAS Discovery: Advancing Life Sciences R&D, 24, 693-700.

12. Grant, E. K., Fallon, D. J., Eberl, H. C., Fantom, K. G., Zappacosta, F., Messenger, C., Tomkinson, N. C. & Bush, J. T. (2019). A photoaffinity displacement assay and probes to study the cyclin-dependent kinase family. Angewandte Chemie International Edition, 58(48), 17322-17327.

13. (a) Catalano, M., Oehler, S., Prati, L., Favalli, N., Bassi, G., Scheuermann, J., & Neri, D. (2020). Complexation with a cognate antibody fragment facilitates affinity measurements of fluorescein-linked small molecule ligands. Analytical Chemistry, 92, 10822-10829 (b) Prati, L., Bigatti, M., Donckele, E. J., Neri, D., & Samain, F (2020). On-DNA hit validation methodologies for ligands identified from DNA-encoded chemical libraries. Biochemical and Biophysical Research Communications. https://doi.org/10.1016/j.bbrc.2020.04.030

14. (a) Jetson, R. R., & Krusemark, C. J. (2016). Sensing Enzymatic Activity by Exposure and Selection of DNA-Encoded Probes. Angewandte Chemie, 128(33), 9714-9718. (b) Kim, D., Jetson, R. R., & Krusemark, C. J. (2017). A DNA-assisted immunoassay for enzyme activity via a DNA-linked, activity-based probe. Chemical Communications, 53(68), 9474-9477.

15. (a) Li, G., Liu, Y., Liu, Y., Chen, L., Wu, S., Liu, Y., & Li, X. (2013). Photoaffinity Labeling of Small-Molecule-Binding Proteins by DNA-Templated Chemistry. Angewandte Chemie International Edition, 52, 9544-9549. (b) Denton, K. E., & Krusemark, C. J. (2016). Crosslinking of DNA-linked ligands to target proteins for enrichment from DNA-encoded libraries. MedChemComm, 7, 2020-2027.

16. Denton, K. E., Wang, S., Gignac, M. C., Milosevich, N., Hof, F., Dykhuizen, E. C., & Krusemark, C. J. (2018). Robustness of in vitro selection assays of DNA-encoded peptidomimetic ligands to CBX7 and CBX8. SLAS DISCOVERY: Advancing Life Sciences R&D, 23, 417-428.

17. Cai, B., Kim, D., Akhand, S., Sun, Y., Cassell, R. J., Alpsoy, A. & Krusemark, C. J. (2019). Selection of DNA-encoded libraries to protein targets within and on living cells. Journal of the American Chemical Society, 141, 17057-17061.

The invention claimed is:

1. An assay kit for small molecule screening to determine apparent affinity constant of a small molecule ligand through ligand displacement comprising:
   a. Instructions for performing an assay using the kit components in high throughput assay,
   b. a DNA-linked probe and
   c. a complementary strand DNA-linked cross-linker,
   d. a free ligand,
   e. a target protein of interest,
   f. wherein said DNA-linked probe comprises a known protein ligand and an electrophilic or photoreactive crosslinker appended at the 5' or 3' end of an encoding DNA;
   g. wherein said protein ligand and said electrophilic or photoreactive crosslinker locate together on one end of said encoding DNA or separately on either 5' or 3' end; and wherein said electrophilic or photoreactive cross-linker is part of said protein ligand or linked to said protein ligand via a chemical linker;

h. and wherein said encoding DNA has a uniquely identified sequence which can be correlated with a specific linked protein ligand.

2. The assay kit according to claim 1, wherein:

a. the instructions for performing the assay calls for the variation of the concentration of the target protein of interest or the free ligand b. which results in a dose dependent variation in crosslinking yield, c. which enables the determination of the apparent affinity constant of said ligand by curve fitting of the data, d. wherein the crosslinking yield is proportional to the affinity constant of the ligand.

3. The assay kit according to claim 1, wherein:

a. the instructions for said assay kit describes use for simultaneous determination of a plurality of compounds' dissociation constants to a protein target, b. where there are more than one independently identifiable DNA-linked probe, c. and where there are more than one independently identifiable complementary-DNA-linked crosslinker.

4. The assay kit according to claim 1, wherein:

a. The instructions for said assay kit describes use for direct determination of a compound's IC50 against multiple protein targets simultaneously, b. where there are more than one independently identifiable DNA-linked probe, c. and where there are more than one independently identifiable complementary-DNA-linked crosslinker.

5. The assay kit according to claim 4, wherein said instructions are for assay in a crude cell lysate.

6. The assay kit according to claim 3, wherein said instructions are for assay for determination of a plurality of compounds' dissociation constants to a protein target simultaneously, and direct determination of a compound's IC50 against multiple protein targets all at once in a crude cell lysate.

7. The assay kit according to claim 1, wherein the instructions for said assay kit is for being configured for generation of structure-activity relationships, and development of selective chemical probes with a high sensitivity.

8. An assay method for small molecule screening to determine apparent affinity constant of a small molecule ligand through ligand displacement or direct binding comprising a. preparing a DNA-linked probe, a complementary strand DNA-linked cross-linker, a free ligand, and a target protein of interest, wherein said DNA-linked probe comprises a known protein ligand appended at the 5' end of an encoding DNA along with an electrophilic or photoreactive crosslinker attached opposite to the ligand on the 3' end of the encoding DNA;

b. applying said free ligand to said target protein, the DNA-linked probe, and the complementary DNA-linked crosslinker in a compatible medium; and c. running the assay, collecting and analyzing the data to afford said assay result information;

d. wherein in a ligand displacement assay, variation of the concentration of the target protein of interest or the free ligand results in a dose dependent variation in crosslinking yield, which enables the determination of the apparent affinity constant of said ligand by curve fitting of the data because the crosslinking yield is proportional to the affinity constant of the ligands;

e. wherein in a direct binding assay, direct determination of a compound's IC50 is determined with reference to the bound ligand; and f. wherein said assay method is capable of being configured for high throughput screening, generation of structure-activity relationships, and development of selective chemical probes with a high sensitivity and a low cost.

9. The assay method according to claim 8, wherein said assay method is capable of being configured for simultaneous determination of a plurality of compounds' dissociation constants to a protein target.

10. A DNA based protein ligand binding assay for characterization of protein-ligand interactions of multiple ligands comprising;

a. incubating a protein target with a DNA-linked probe, wherein the DNA-linked probe comprises a known protein ligand appended at the 5' end of an encoding DNA along with an electrophilic crosslinker or photo reactive group appended to the same end or opposite end from the ligand, such that the DNA-linked probe can be crosslinked to the target protein;

b. where the electrophilic crosslinker is selected from the group of sulfonyl fluoride or N-hydroxysuccinimide ester, and the photoreactive group is selected from diazirine or aryl azide benzopenome;

c. where multiple assay samples are screened as a pool, by using multiple DNA-linked probes, each of which has a distinct DNA sequence which becomes a barcode to encode the identity of that specific probe ligand;

d. following incubation to allow crosslinking, labeling by the probe is quenched by addition of excess free ligand, e. wherein co-incubation with a competing free ligand will displace the DNA-linked probe, resulting in decreased affinity labeling of the protein and lower DNA recovery in subsequent purification and isolation of the protein;

f. collected components from all samples are pooled;

g. target protein is then purified;

h. the relative recovery of each DNA probe is determined by DNA sequencing and indicates the crosslinking yield in each sample, where a dose dependent reduction in crosslinking is observed as the concentration of free ligand increases, enabling the calculation of IC50 values.

\* \* \* \* \*